United States Patent [19]

Wirth et al.

[11] Patent Number: 4,830,770

[45] Date of Patent: May 16, 1989

[54] HYDRAULIC FLUID COMPOSITIONS, NOVEL GLUCAMINE DERIVATIVES AND COMPLEX COMPOUNDS CONTAINING SAME

[75] Inventors: Hermann O. Wirth, Bensheim; Hans-Helmut Friedrich, Lautertal, both of Fed. Rep. of Germany

[73] Assignee: Ciba-Geigy Corporation, Ardsley, N.Y.

[21] Appl. No.: 137,269

[22] Filed: Dec. 23, 1987

Related U.S. Application Data

[62] Division of Ser. No. 876,953, Jun. 20, 1986, Pat. No. 4,732,691.

[30] Foreign Application Priority Data

Jun. 21, 1985 [CH] Switzerland ............. 2648/85
Jul. 2, 1985 [CH] Switzerland ............. 2818/85

[51] Int. Cl.$^4$ ........................... C10M 129/04
[52] U.S. Cl. ..................... 252/77; 252/51.5 A; 252/51.5 R
[58] Field of Search ............ 252/47.5, 51.5 A, 51.5 R, 252/77

[56] References Cited

U.S. PATENT DOCUMENTS

| | | | |
|---|---|---|---|
| 2,856,363 | 10/1958 | Brennan | 252/51.5 A |
| 3,872,116 | 3/1975 | Gyson | 252/392 |
| 4,549,882 | 10/1985 | Knapp | 44/53 |
| 4,551,257 | 11/1985 | Horodysky | 252/51.5 |
| 4,732,691 | 3/1988 | Wirth et al. | 252/47.5 |

*Primary Examiner*—Jacqueline V. Howard
*Attorney, Agent, or Firm*—Harry Falber

[57] ABSTRACT

The invention relates to compositions comprising a lubricant or a hydraulic fluid and at least one compound of the general formula

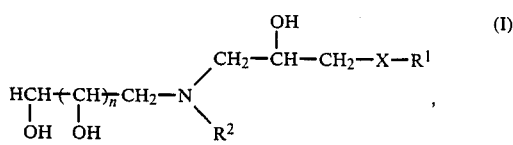

(I)

wherein n is 2, 3 or 4, X is —S—, —O—, —O—CO— or —CH$_2$—, R$^1$ is C$_1$-C$_{22}$alkyl, C$_5$-C$_6$cycloalkyl or phenyl, and R$^2$ is hydrogen, C$_1$-C$_8$alkyl, C$_2$-C$_4$alkyl which is substituted by an —OH group, or a group of the formula —CH$_2$—CH(OH)—CH$_2$—X—R$^1$, wherein X and R$^1$ have the given meanings, and to novel compounds of the formula indicated above. The glucamine derivatives of formula I are especially suitable for use as antiwear agents and as extreme pressure additives for mineral and synthetic lubricant oils and hydraulic fluids, and also as amphipolar ligands for imparting lipophilic properties to intrinsically hydrophilic metal salts, metal oxides, metal hydroxides and to protic acids. The complex compounds so obtained of the formula $$M_n{}^m \cdot X_m{}^n \cdot pY \cdot qZ,$$

wherein M is a cation of valency m or a proton, X is an anion of valency n, Z is a compound of formula I, Y is water or a neutral organic molecule, p is a value from 0 to 2, q is a value from 1 to 8, m is an integer from 1 to 6 and n is an integer from 1 to 4, are also disclosed.

7 Claims, No Drawings

HYDRAULIC FLUID COMPOSITIONS, NOVEL GLUCAMINE DERIVATIVES AND COMPLEX COMPOUNDS CONTAINING SAME

This is a division of application Ser. No. 876,953, filed on June 20, 1986, now U.S. Pat. No. 4,732,691.

The present invention relates to novel glucamine derivatives, to lubricants and hydraulic fluids containing glucamine derivatives as additives, to complex compounds containing such glucamine derivatives and to the use thereof as additives for plastics and lubricants.

Glucamine derivatives and the preparation thereof are disclosed as additives for cosmetic compositions in e.g. U.S. Pat. No. 4,281,201 and Japanese published patent applications Nos. 79/135,233 and 79/163,829. However, glucamine derivatives as additives for lubricants have not yet been disclosed.

Stringent demands are made of lubricant additives. In particular, they must improve the stability of the lubricant to oxidative degradation at elevated temperature, they must increase the load carrying properties and they must ensure their suitability at elevated temperature in the presence of materials that are susceptible to corrosion. Finally, a most essential requirement is also to enhance the antiwear properties of these lubricants.

It has been possible to develop compounds that impart excellent extreme pressure and, in particular, antiwear, properties to lubricants.

Accordingly, the present invention relates to compositions comprising a lubricant or hydraulic fluid and at least one compound of the general formula I

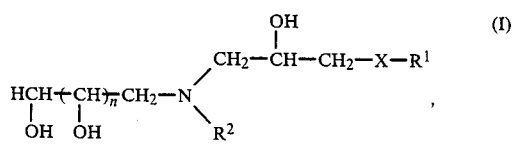

wherein n is 2, 3 or 4, X is —S—, —O—, —O—CO— or —CH$_2$—, R$^1$ is C$_1$–C$_{22}$alkyl, C$_5$–C$_6$cycloalkyl or phenyl, and R$^2$ is hydrogen, C$_1$–C$_8$alkyl, C$_2$–C$_4$alkyl which is substituted by an -OH group, or a group of the formula —CH$_2$—CH(OH)—CH$_2$—X—R$^1$, wherein X and R$^1$ have the given meanings.

The preferred meaning of X is —O—, —CH$_2$— or —S—, with —S— being particularly preferred. If X is —O—CO—, the carbonyl—C atom is attached to the radical R$^1$.

R$^1$ as C$_1$–C$_{22}$alkyl is a straight chain or branched C$_1$–C$_{22}$alkyl substituent which may be selected from the group consisting of methyl, ethyl, n-propyl, isopropyl, n-butyl, sec-butyl or tert-butyl, pentyl, 1-methylpentyl, n-hexyl, 2-ethyl-n-hexyl (isooctyl), n-heptyl, 1-methylheptyl, straight chain or branched octyl, nonyl, decyl, undecyl, dodecyl, tridecyl, tetradecyl, pentadecyl, hexadecyl, octadecyl, eicosyl or docosyl. Tertiary alkyl radicals are especially preferred.

R$^1$ is preferably straight chain or branched C$_1$–C$_4$alkyl and, most preferably, C$_5$–C$_{18}$alkyl, with C$_8$–C$_{12}$alkyl being particularly preferred.

In a particularly preferred embodiment of the compositions of the present invention, R$^1$ in compounds of formula I is tert-nonyl or tert-dodecyl, with tert-dodecyl being understood as meaning e.g. a radical as defined for tertiary dodecylmercaptan in Ullmanns Enzyklopädie der technischen Chemie, 4th Edition, pp. 181–182, Verlag Chemie, Weinheim, so that X is attached to a tertiary carbon atom.

If the radicals R$^1$ and X occur more than once in the compounds of formula I, then they may be identical or different, preferably identical, radicals.

R$^2$ as C$_1$–C$_8$alkyl may be methyl, ethyl, isopropyl, n-propyl, n-butyl or sec-butyl, 2-ethyl-n-hexyl or n-octyl, with methyl or ethyl being preferred. R$^2$ as C$_2$–C$_4$alkyl which is substituted by an —OH group may be 2-hydroxyethyl, 2-hydroxypropyl, 3-hydroxypropyl or 2-hydroxybutyl, with 2-hydroxethyl being preferred. Further, R$^2$ is preferably a group of the formula —CH$_2$—CH(OH)—CH$_2$—X—R$^1$, wherein X and R$^1$ have the meanings assigned to them above.

n is an integer having the value 2, 3 or preferably 4.

Preferred compositions are those comprising a lubricant or a hydraulic fluid and at least one compound of formula I, wherein X is —S—, —CH$_2$— or —O—, R$^1$ is straight chain or branched C$_5$–C$_{16}$alkyl, R$^2$ is methyl, ethyl or a group of the formula —CH$_2$—CH(OH)—CH$_2$—X—R$^1$, wherein X and R$^1$ have the given meanings, and n is 4.

Some of the compounds of formula I are novel. Hence the invention also relates to compounds of formula I, wherein n is 2, 3 or 4, X is —S—, —O— or —O—CO—, R$^1$ is C$_1$–C$_{22}$alkyl and R$^2$ is a group of the formula —CH$_2$—CH(OH)—CH$_2$—X—R$^1$, wherein X and R$^1$ have the given meanings or, if X is —S—, R$_2$ is also hydrogen, C$_1$–C$_8$alkyl or C$_2$–C$_4$alkyl which is substituted by an —OH group. The preferred meanings of X, R$^1$, R$^2$ and n are those stated above.

Examples of compounds of formula I are:

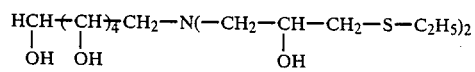

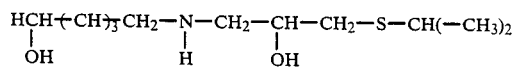

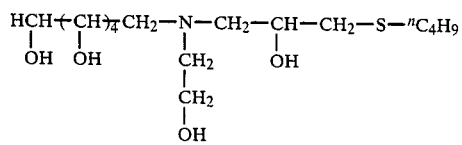

-continued

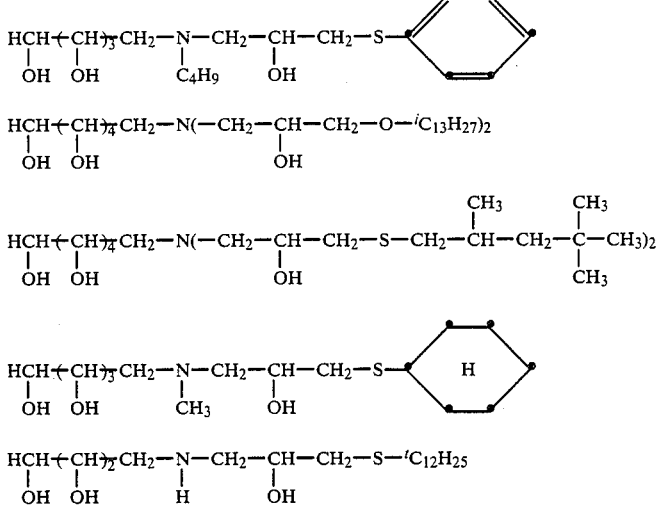

The compounds of formula I can be prepared in a manner known per se, for example by reacting suitable glucamines of formula III

wherein n has the given meaning and Z is hydrogen, $C_1$–$C_8$alkyl, or $C_2$–$C_4$alkyl which is substituted by an —OH group, with glycidyl compounds of formula

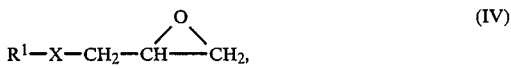

wherein X and $R^1$ have the given meanings. Where Z=H, at least 2 moles of IV are used per mole of III; but where Z is not hydrogen, it is convenient to use approximately equimolar amounts.

The glucamines of formula III can be obtained in a manner which is known per se, e.g. by reacting a suitable monosaccharide with a suitable primary amine and subsequently reducing the reaction product. The glycidyl compounds of formula IV are known or they can be readily obtained by conventional methods.

The compounds of formula I are in general liquid or viscous fluids. Individual compounds of formula I are highly viscous or resinous or tarry substances and may be used, where necessary, for ease of handling in highly concentrated form in water or a suitable base oil.

The glucamine derivatives of this invention constitute lubricant additives which are distinguished by good extreme pressure and, in particular, antiwear properties. Even when incorporated in very small amounts, the compounds of formula I are effective in lubricants and hydraulic fluids, to which end a sufficient solubility in the respective substrate is a prerequisite. Thus mineral and synthetic lubricant oils and mixtures thereof, as well as hydraulic fluids, which contain e.g. 0.01 to 5% by weight, preferably 0.05 to 3% by weight, based on said lubricant, of a compound of formula I have excellent properties, especially extreme pressure properties, which are apparent from the reduced wear of the parts to be lubricated. The suitable lubricants are known to the skilled person and are described e.g. in "Schmierstoffe und verwandte Produkte" (Verlag Chemie, Weinheim, 1982).

The additives of formula I are particularly suitable for use in non-automatic and, first and foremost, in automatic transmissions of automobiles. Further, they are most effective in motor oils, diesel engine oils or turbine oils.

The lubricant compositions of this invention may contain other additives which are incorporated to enhance the basic properties of lubricants still further. These further additives comprise: antioxidants, metal deactivators, rust inhibitors, viscosity index improvers, pour-point depressors, dispersants, surfactants and other extreme pressure additives and antiwear additives.

Examples of phenolic antioxidants

1. Alkylated monophenols
2,6-di-tert-butyl-4-methylphenol
2,6-di-tert-butylphenol
2-tert-butyl-4,6-dimethylphenol
2,6-di-tert-butyl-4-ethylphenol
2,6-di-tert-butyl-4-n-butylphenol
2,6-di-tert-butyl-4-sec-butylphenol
2,6-dicyclopentyl-4-methylphenol
2-(α-methylcyclohexyl)-4,6-dimethylphenol
2,6-di-octadecyl-4-methylphenol
2,4,6-tricyclohexylphenol
2,6-di-tert-butyl-4-methoxymethylphenol o-tert-butylphenol 2. Alkylated hydroquinones
2,6-di-tert-butyl-4-methoxyphenol
2,5-di-tert-butyl-hydroquinone
2,5-di-tert-amyl-hydroquinone
2,6-diphenyl-4-octadecyloxyphenol 3. Hydroxylated thiodiphenyl ethers
2,2'-thio-bis(6-tert-butyl-4-methylphenol)
2,2'-thio-bis(4-octylphenol)
4,4'-thio-bis(6-tert-butyl-3-methylphenol)
4,4'-thio-bis(6-tert-butyl-2-methylphenol)

4. Alkylidene bisphenols
2,2'-methylene-bis(6-tert-butyl-4-methylphenol)
2,2'-methylene-bis(6-tert-butyl-4-ethylphenol)
2,2'-methylene-bis[4-methyl-6-(α-methylcyclohexyl)-phenol]

2,2'-methylene-bis-(4-methyl-6-cyclohexylphenol)
2,2'-methylene-bis-(6-nonyl-4-methylphenol)
2,2'-methylene-bis(4,6-di-tert-butylphenol)
2,2'-ethylidene-bis(4,6-di-tert-butylphenol)
2,2'-ethylidene-bis(6-tert-butyl-4-isobutylphenol)
2,2'-methylene-bis[6-(α-methylbenzyl)-4-nonylphenol]
2,2'-methylene-bis[6-(α,α-dimethylbenzyl) -4-nonylphenol]
4,4'-methylene-bis-(2,6-di-tert-butylphenol)
4,4'-methylene-bis(6-tert-butyl-2-methylphenol)
1,1-bis-(5-tert-butyl-4-hydroxy-2-methylphenyl)-butane
2,6-di-(3-tert-butyl-5-methyl-2-hydroxybenzyl)-4-methylphenol
1,1,3-tris-(5'-tert-butyl-4'-hydroxy-2'-methylphenyl)-3-n-dodecylmercaptobutane
ethyleneglycolbis[3,3-bis-(3'-tert-butyl-4'-hydroxyphenyl)-butyrate]
di-(3-tert-butyl-4-hydroxy-5-methylphenyl)-dicyclopentadiene
di-[2-(3'-tert-butyl-2'-hydroxy-5'-methylbenzyl)-6-tert-butyl-4-methylphenyl]terephthalate.

5. Benzyl compounds 1,3,5-tri-(3',5'-di-tert-butyl-4'-hydroxybenzyl)-2,4,6-trimethylbenzene
di-(3,5di-tert-butyl-4-hydroxybenzyl)sulfide
bis-(4-tert-butyl-3-hydroxyl-2,6-dimethylbenzyl)dithiol-terephthalate
1,3,5-tris(3',5'-di-tert-butyl-4'-hydroxybenzyl)isocyanurate
1,3,5-tris-(4'-tert-butyl-3'-hydroxy-2',6'-dimethylbenzyl)-isocyanurate
diocotadecyl 3,5-di-tert-butyl-4-hydroxybenzylphosphate
calcium salt of monoethyl 3,5-di-tert-butyl-4-hydroxybenzylphosphonate 6. Acylaminophenols
4-hydroxylauric anilide
4-hydroxystearic anilide
2,4-bisoctylmercapto-6-(3',5'-tert-butyl-4'-hydroxyanilino)-s-triazine
octyl-N-(3,5-di-tert-butyl-4-hydroxyphenyl)carbamate 7. Esters of β-(3,5-di-tert-butyl-4-hydroxyphenyl)propionic acid
with monohydric or polyhydric alcohols, for example with methanol, octadecanol, 1,6-hexanediol, neopentyl glycol, thiodiethylene glycol, diethyleneglycol, triethylene glycol, pentaerythritol, trishydroxyethyl isocyanurate, dihydroxyethyloxalyldiamide.

8. Esters of β-(5-tert-butyl-4-hydroxy-3-methylphenyl)-propionic
acid with monohydric or polyhydric alcohols, for example methanol, octadecanol, 1,6-hexanediol, neopentylglycol thiodiethyleneglycol, diethylene glycol, triethyleneglycol pentaerytritol, trishydroxyethyl isocyanurate or dihydroxyethyloxalyldiamide.

9. Amides of β-(3,5-di-tert-butyl-4-hydroxyphenyl)propionic acid
for example,
N,N'-bis(3,5-di-tert-butyl-4-hydroxyphenylpropionyl)-hexamethylenediamine
N,N'-bis(3,5-di-tert-butyl-4-hydroxyphenylpropionyl)-trimethylenediamine
N,N'-bis(3,5-di-tert-butyl-4-hydroxyphenylpropionyl)-hydrazine.

Examples of amine antioxidants

N,N'-diisopropyl-p-phenylenediamine
N,N'-di-sec-butyl-p-phenylenediamine
N,N'-bis(1,4-dimethypentyl)-p-phenylenediamine
N,N'-bis(1-ethyl-3-methylpentyl)-p-phenylenediamine
N,N'-bis(1-methylheptyl)-p-phenylenediamine
N,N'-diphenyl-p-phenylenediamine
N,N'-di(naphthyl-2-)-p-phenylenediamine
N-isopropyl-N'-phenyl-p-phenylenediamine
N-(1,3-dimethylbutyl)-N'-phenyl-p-phenylenediamine
N-(1-methylheptyl)-N'-phenyl-p-phenylenediamine
N-cyclohexyl-N'-phenyl-p-phenylenediamine
bis-4-(toluenesulfonamidophenyl)amine
N,N'-dimethyl-N,N'di-sec-butyl-p-phenylenediamine
diphenylamine
4-isopropoxydiphenylamine
N-phenyl-1-naphthylamine
N-phenyl-2-naphthylamine
octylated diphenylamine
4-n-butylaminophenol
4-n-butyrylaminophenol
4-nonanoylaminophenol
4-dodecanoylaminophenol
4-octadecanoylaminophenol
di-(4-methoxyphenyl)amine
2,6-di-tert-butyl-4-dimethylaminomethylphenol
2,4-diaminodiphenylmethane
4,4'-diaminodiphenylmethane
N,N,N'N'-tetramethyl-4,4'-diaminodiphenylmethane
1,2-di(phenylamino)ethane
1,2-di-[(2-methylphenyl)amino]ethane
(o-tolyl)biguanide
di-[4-(1',3'-dimethylbutyl)phenyl]amine
tert-octylated N-phenyl-1-naphthylamine
mixture of mono- and dialkylated tert-butyl- and tert-octyldiphenylamines Examples of metal deactivators are for copper, e.g.: benzotriazole, tetrahydrobenzotriazole, 2-mercaptobenzotriazole, 2,5-dimercaptothiadiazole, salicylidene propylenediamine, salts of salicylaminoguanidine.

Examples of rust inhibitors are (a) Organic acids, the esters, metal salts and anhydrides thereof, e.g.: N-oleylsarcosine, sorbitan monooleate, lead naphthenate, dodecenylsuccinic anhydride, monoalkenyl succinate, 4-nonylphenoxyacetic acid.
(b) Nitrogen-containing compounds, for example:
  I. Primary, secondary or tertiary aliphatic or cycloaliphatic amines and amine salts of organic and inorganic acids, for example oil-soluble alkylammonium carboxylates.
  II. Heterocyclic compounds, e.g. substituted imidazolines and oxazolines.
(c) Phosphorous-containing compounds, for example: amine salts of phosphoric acid partial esters.
(d) Sulfur-containing compounds, for example: barium dinonylnaphthalenesulfonates, calcuim petroleum sulfonates.

Examples of viscosity index improvers are polymethylacrylates, vinyl pyrrolidone/methacrylate copolymers, polybutene, olefin copolymers, styrene/acrylate copolymers.

Examples of pour-point depressors are polymethacrylates, alkylated naphthalene derivatives.

Examples of dispersants/surfactants are polybutenylsuccinimides, polybutenylphosphonic acid derivatives, basic magnesium, calcium and barium sulfonates and phenolates.

Examples of anti-wear additives are compounds which contain sulfur and/or phosphorous and/or halogen, such as sulfurised vegetable oils, zinc dialkyldithiophosphates, tritolylphosphate, chlorinated paraffins, alkyl disulfides and aryl disulfides.

The compounds of formula I are furthermore preeminently suitable as amphipolar ligands for imparting lipophilic properties (complexing) to intrinsically hydrophilic metal and semi-metal salts, metal and semi-metal hydroxides, metal and semi-metal oxides and to protic acids. Hence they may be used in the practice of this invention for solubilising intrinsically hydrophilic, preferably inorganic, compounds for use in hydrophobic systems.

Complex compounds of metal and semi-metal salts as well as protic acids of specific diols and triols are disclosed in U.S. Pat. Nos. 4,336,148 and 4,404,408, by means of which compounds the lipophilic properties of the cited salts or acids can likewise be modified. Particularly stable complex compounds with a wide range of utilities are obtained by complexing such hydrophilic compounds with the compounds of formula I. Surprisingly, the complexes have even better solubility in hydrophobic systems, and fewer amphipolar ligands are required for imparting lipophilic properties than in the case of the known complexes.

The present invention therefore also relates to complex compounds of a metal salt, semi-metal salt, metal or semi-metal hydroxide, metal or semi-metal oxide or of a protic acid of the general formula II

   (II)

wherein

M is a cation of valency m of a metal or semi-metal cation or is an oxymetal or dioxymetal cation or a proton, X is an anion of valency n of an n-basic inorganic protic acid or of an n-basic organic acid selected from the group consisting of aliphatic and cycloaliphatic carboxylic acids containing up to 8 carbon atoms and which may be substituted by halogen atoms and/or hydroxyl groups, of aromatic mono-, di- and tricarboxylic acids which may be substituted by hydroxyl groups, halogen atoms and/or nitro groups, of organic oxyacids of phosphorus and sulfur, of organic thioacids of phosphorus, and from the group of the mercaptans, said inorganic or organic acids having a $pK_a$ value of not more than 15.8 and, if M is a proton, of not more than 11, or $X^n$ is —OH or O, Y is water or a neutral organic molecule which is co-ordinatively bonded to the cation or to the anion, Z is a compound of formula I p is a value from 0 to 2, q is a value from 1 to 8, m is an integer from 1 to 6, and n is an integer from 1 to 4.

The cation of valency m is preferably derived from a metal of Periodic Groups 1a to 8a and 1b to 5b, from the lanthanides, uranium, plutonium or from the semi-metals boron, silicon, germanium and antimony. The valency m of the cation derives from the position of the elements in the Periodic Table. In this specification, the valency will be understood as meaning the number m of electrons which a metal is able to donate to form a metal ion carrying a charge m. As is common knowledge, an element is able to exist in different stable valency states, e.g. tin can be divalent or tetravalent, chromium can be divalent or trivalent, or copper can be univalent or divalent. Tungsten hexafluoride has for example valency 6. The valency m is preferably 1 to 5, most preferably 1 to 3.

The cation is preferably derived from the following elements: Li, Na, K, Be, Mg, Ca, Sr, Ba, Al, Sc, La, Ce, Eu, Ti, Zr, Hf, Th, V, Nb, Ta, Cr, Mo, W, U, Mn, Fe, Co, Ni, Rh, Pd, Os, Jr, Pt, Cu, Ag, Au, Zn, Cd, Hg, Sn, Pb, Bi, and from the semimetals B, Si, Ge and Sb.

More preferably, the cation is derived from the metals of the group consisting of Li, Na, K, Mg, Ca, Sr, Ba, Al, Ti, Zr, V, Cr, Mo, W, Mn, Fe, Co, Ni, Cu, Ag, Au, Zn, Cd, Sn, Pb, and Bi and from the semimetals B, Si and Sb.

Most preferably, M is hydrogen, Na, K, Mg, Ca, Sr, Ba, Al, Cr, Mn, Fe, Co, Ni, Cu, Ag, Zn, Cd, Hg, Sn, Pb, B oder Si, especially Ca, Ba, Cu, Ni, Fe or Co.

A number of metals are also able to form oxymetal cations which contain one or two oxygen atoms. Among these cations, titanyl, vanadyl, zirconyl and uranyl are preferred. The tetravalent cation tungstenyl and the univalent cations antimonyl and bismuthyl may also be mentioned.

The inorganic acid and the previously defined organic acids from which the anion is derived preferably have a $pK_a$ value not greater than 10, preferably not greater than 4. The $pK_a$ value of the strongest acids is up to about $-10$. As is common knowledge, the $pK_a$ value, which is a measure of the strength of acids, is defined for protolytes in aqueous systems as the negative decadic logarithm of the equilibrium constant of the protolysis reaction. The same definition also applies to the $pK_b$ value, which is a measure of the strength of bases. It has been found that those complexed compounds of formula II which are derived from strong acids are particularly stable. The upper limit of the $pK_a$ value of 15.8 also includes water as weak acid. The radical X will also be understood as meaning the the oxo radical O=.

X is the anion of an n-basic inorganic or organic protic acid as defined above, or the radical O. This definition also encompasses protic acids which do not exist in the free form but only in the form of their salts, e.g. the ammonium salts. The basicity n indicates the number of negative charges which are formed in the anion by the removal of n protons. In addition to the anions of monobasic acids such as hydrochloric acid, anions of tetrabasic acids are also known, e.g. silicate or titanate, so that n is an integer from 1 to 4. X also encompasses polymeric anions, e.g. those of the silicates, titanates, phosphates, arsenates, zirconates, vanadates, borates, molybdates, tungstenates and antimonates.

The anion X is preferably derived from inorganic protic acids selected from the group of the hydrohalic and pseudohydrohalic acids and hydroselenic acid, inorganic oxyacids or thioacids, and of the inorganic complex acids. Typical examples of the pseudohydrohalic acids are: HF, HCl, HBr, HI, HCN, HCNO, HCNS and HN$_3$.

The inorganic oxyacids are preferably derived from the elements C, N, P, As, S, Se, Cl, Br and I, or from the amphoteric elements and the semi-metals. The inorganic thioacid is preferably H₂S or is derived from the elements C, V, Mo, W, Sn, P, As, Sb and S.

Representative examples of anions of oxyacids of the cited elements are: carbonate, bicarbonate, nitrite, nitrate, hypophosphite, phosphite, orthophosphate, polyphosphates such as diphosphates, metaphosphates such as metaphosphate, trimetaphosphate or tetrametaphosphate, fluorophosphate, arsenite, arsenate, sulfite, sulfate, peroxomonosulfate, peroxodisulfate, thiosulfate, dithionite, dithionate, pyrosulfite, pyrosulfate, polythionate, fluorosulfate, selenite, selenate, tellurite, tellurate, hypochlorite, chlorite, chlorate, perchlorate, bromite, bromate, iodate, periodate.

In addition to sulfide, anions of thioacids are: polysulfides such as disulfide, thiocarbonate, dithiocarbonate, trithiocarbonate, thiovanadate, thiomolybdate, thiotungstenate, thiostannate, thioantimonate, thioarsenate, thioarsenite, thioantimonite, trithiophosphate, tetrathiophosphate and trithiophosphite.

Representative examples of oxyacids of the amphoteric elements and semi-metals are: borate, metaborate, silicate, metasilicate, germanate, antimonite, antimonate, aluminate, titanate, zirconate, vanadate, chromate, dichromate, molybdate, tungstenate, manganate, permanganate, stannite and stannate.

By anions of inorganic complex acids are meant those comprising a central metal or semi-metal atom and chelating acidoligands. Examples of suitable metals and semi-metals are: B, Si, Ge, As, Sb, Al, Ti, Zr, V, Nb, Ta, Cr, Mo, W, Mn, Zn, Cd, Fe, Co, Ni, Ru, Rh, Pd, Os, Ir, Pt, Cu, Ag, Au, Sn, Pb and Bi. Examples of suitable acido-ligands are the halides, preferably fluoride and chloride, the pseudohalides, preferably cyanide and thiocyanide, the —CO group and oxalate. These complex anions belong principally to the $[MX'_4]^n$, $[MX'_5]^n$ and $[MX'_6]^n$ types, wherein M is the metal or semi-metal ion, X' is the acidoligand and n is the basicity (negative charge) resulting from the valency of the metal or semi-metal and from the charge of the acidoligand. It should also be mentioned that, among the many complex anions, polynuclear anions are also known. Examples are: tetrafluoroborate, hexafluorosilicate, hexafluoroarsenate, hexafluoroantimonate, pentafluoroantimonate (III), hexafluorophosphate, tetrafluoroaluminate, hexafluoroaluminate, hexafluorotitanate, hexafluoromolybdate or hexafluorowolframate, hexafluorochromate (III), hexafluoroferrate, hexafluorocobalate, hexafluoroplatinate, tetrafluorozincate, hexafluorostannate, hexafluoroplumbate, hexafluoromanganate, hexafluororhodinate, hexachloroiridiumate, hexafluorotantalate oder hexafluoro niobate, tetrachloroaluminate, hexachlorotitanate, hexachlorovanadate, tetrachlorovanadate, hexachlorochromate, hexachloromanganate, hexachloromolybdate and hexachlorofungstenate, hexachloroferrate, tetrachloronickelate, hexaiodotechnate, hexachlororehnate, hexachlororhutenate, hexachloroosmate, hexachlorostannate, hexachloroplumbate, hexachloroantimonate, hexachlorobismuthate, tetrabromocadmiumate, tetracyanozincate, tetrachloro, tetrabromo or tetraiodomercurate, tetracyanomercurate, tetrathiocyanatomercurate, hexacyanovanadate, trioxalatovanadate, hexacyanochromate, trioxalatochromate, pentacyanonitrosochromate, hexacyanomanganate, hexathiocyanatomanganate, trioxalatomanganate, hexacyanoferrate, tetracyanocobaltate, tetracyanonickelate, tetracyanocuprate, tetraoxalatozirconate, hexarhodanomolybdate, octacyanomolybdate, octacyanotungstenate, octacyanorehnate, hexacyanoplatinate, hexacyanoosmate, tetracyanopalladiumate, pentacarbonylmanganate, tetracarbonylferrate, tetracarbonylcobaltate.

A number of the complex acids are known in the free form, whereas others are known only in the form of their salts, e.g. of the ammonium salts.

X can also be the anion of an n-basic aliphatic or cycloaliphatic carboxylic acid containing not more than 8, preferably 1 to 4, carbon atoms and which may be substituted by halogen or hydroxyl. The carboxylic acid is preferably substituted in the α-position, in particular by fluorine, chlorine or bromine, and is preferably monobasic or dibasic. Examples of such anions are: formate, acetate, propionate, butyrate, oxalate, malonate, succinate, fumarate, maleinate, dithiopropionate, hydroxyacetate, mono-, di- and tribromoacetate or mono-, di- and trichloroacetate, α-chloropropionate, α-chloromalonate or α-bromomalonate, 1,2-dichlorosuccinate or 1,2-dibromosuccinate.

X can also be the anion of an aromatic carboxylic acid containing preferably not more than 12 carbon atoms and which is preferably selected from the groups consisting of the mono- to tribasic benzene and naphthalene acids, and which may be substituted by halogen atoms, preferably fluorine, chlorine or bromine atoms, or by nitro groups. Examples of such anions are: benzoate, isophthalate, terephthalate, 2-naphthenate, 2,6-dinaphthenate, chlorobenzoate and nitrobenzoate.

X can also be the anion of an organic oxyacid of phosphorus and sulfur and of an organic thioacid of phosphorus. Such acids are preferably phosphonic, phosphinic, thiophosphonic, thiophosphinic, sulfonic and sulfinic acid. The acids of phosphorus may be represented by the following general formula:

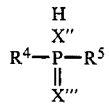

wherein R⁴ is a hydrocarbon radical of aliphatic or aromatic character containing preferably up to 18, most preferably up to 8, carbon atoms and which may be substituted by halogen, preferably fluorine or chlorine, each of X'' and X''' independently is oxygen or sulfur and R⁵ is the —X''H group or hydrogen or independently has the same meaning as R⁴.

The oxyacids of sulfur may be represented by the formula

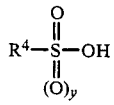

wherein R⁴ is as defined above and y is 0 or 1. R⁴ can be linear or branched alkyl, cycloalkyl, aryl or aralkyl, each of which may be substituted by fluorine or chlorine or alkyl of 1 to 6 carbon atoms. Cycloalkyl is preferably cyclohexyl and aryl and aralkyl are preferably derived from phenyl and naphthyl respectively.

Examples of such radicals are: methyl, ethyl, propyl, butyl, isobutyl, octyl, octadecyl, phenyl, naphthyl, p-methylphenyl, butylphenyl, dibutylphenyl, hexylphenyl, chloromethyl, chloroethyl, chlorophenyl, fluoromethyl, trifluoromethyl.

X can also be the anion of a mercaptan which preferably contains not more than 18, most preferably not more than 12, carbon atoms. The mercaptan preferably has the formula

wherein $R^6$ is linear or branched alkyl which may be interrupted by oxygen, or is hydroxyalkyl, alkoxycarbonylalkyl, phenyl or phenyl which is substituted by $C_1$-$C_{12}$alkyl. Examples of such radicals are: methyl, ethyl, propyl, hexyl, octyl, decyl, dodecyl, octadecyl, β-hydroxyethyl, β-hydroxypropyl, alkoxycarbonylmethyl and β-alkoxycarbonylethyl such as isooctoxycarbonylmethyl or isooctoxycarbonylethyl, phenyl and nonyphenyl.

The anion X can also be derived from dibasic to tetrabasic oxyacids which are partially esterified, preferably with $C_1$-$C_{12}$alkanols or phenols.

Also falling within the scope of the present invention are mixtures which contain a complex compound of formula II, wherein X is an anion as previously defined, as well as one or more compounds of formula II, wherein X is an alcoholate anion. The alkanolate anion may be derived from an alkanol or phenol of preferably 1 to 8 carbon atoms, in which case X may also simultaneously be an alcoholate anion derived from a complexing compound of formula I. Preferably X is solely the last mentioned alcoholate anion. These mixtures are obtained by reacting a metal alcoholate or semi-metal alcoholate derived from the aforementioned alcohols and an at least divalent metal or semi-metal with an excess of an anhydrous compound of formula $H_nX^n$ or with an ammonium salt of formula $A_nX^n$. This reaction affords random mixtures whose composition is largely determined by the amount of the excess. This mixture may also contain still unreacted starting material. Provided X is to be an alkanolate or phenolate anion, a reaction product of a metal or semi-metal alcoholate or phenolate will conveniently be reacted with an excess of a complexing compound of formula I.

A representative number of preferred radicals X are: oxide, hydroxyl, fluoride, chloride, bromide, iodide, cyanide, cyanate, thiocyanide, azide, perchlorate, bromate, iodate, periodate, permanganate, sulfide, hydrosulfide, hydrodifluoride, nitrite, nitrate, sulfite, sulfate, thiosulfate, bisulfate, fluorosulfate, bisulfite, phosphate, hydrophosphate, phosphite, hypophosphite, polyphosphate, monofluorophosphate, carbonate, bicarbonate, thiocarbonate, dithiocarbonate, trithiocarbonate, carbamate, xanthogenate, trithiophosphate, tetrathiophosphate, trithiophosphite, silicate, metasilicate, titanate, borate, metaborate, molybdate, vanadate, aluminate, chromate, dichromate, selenate, tungstenate, arsenite, arsenate, antimonate, stannate, thioarsenite, thioarsenate, thioantimonate, thiostannate, thiomolybdate, thiotungstenate, tetrafluoroborate, hexafluorosilicate, hexafluorotitanate, hexafluoroaluminate, hexachlorostannate, hexachloroferrate, hexacyanoferrate, octacyanomolybdate, hexafluoroantimonate, hexacyanochromate, tetracyanonickelate, trioxalatomanganate, methylphosphonate, methylphosphinate, phenylphosphonate, tosylate, phenylsulfonate, methylsulphinate, formate, acetate, propionate, benzoate, terephthalate, trifluoroacetate, trichloroacetate, chlorobenzoate, trifluoromethylsulfonate, oxalate, malonate, maleinate, fumarate, hydroxyacetate, naphthylsulfonate, dithiodipropionate, methylmercaptide, phenylmercaptide, octoxycarbonylmethylmercaptide, β-hydroxyethylmercaptide.

Particularly preferred radicals X are: oxide, hydroxy, fluoride, bromide, iodide, cyanide, sulfide, hydrosulfide, nitrate, sulfite, sulfate, bisulfate, phosphate, phosphite, hydrophosphate, metaphosphate, polyphosphate, carbonate, bicarbonate, silicate, metasilicate, formate, acetate and oxalate, with chloride, hydrophosphate, phosphate and sulfate being most preferred.

In the compounds of formula II, those anions of formula II are especially preferred which are derived from inorganic acids preferably having a $pK_a$ value not greater than 7.5, and the anions of organic acids having a $pK_a$ value not greater than 4. If M is a proton, the $pK_a$ value is preferably not greater than 9.5, most preferably not greater than 4.

Y as water may form a co-ordinate bond with the cation or also anion in the compounds of formula II, i.e. it can be in the form of water of crystallisation. It is sometimes not possible for the water to be removed completely. The preferably contain no or only very little water.

Y can also be an organic molecule which may form a co-ordinate bond and is preferably an alcohol, an ether, an acid amide, a sulfoxide or a sulfone, e.g. methanol, ethanol, diethyl ether, tetrahydrofuran, dimethylformamide, dimethylsulfone or tetramethylsulfone. The complex compounds of formula II may contain insignificant residual amounts of these compounds if they are prepared in the corresponding solvents.

Normally, however, water and the organic compounds referred to above can be removed almost completely, so that p is preferably a value from 0 to 1, most preferably 0.

The value of q indicates the number of complex forming molecules of formula I in the compounds of formula II. The value of q is preferably 1 to 4, especially 1 or 2, and is most preferably 1.

Compounds of formula II can be prepared by methods identical or similar to those disclosed in German Offenlegungsschrift specification No. 2 330 906 or U.S. Pat. Nos. 4,404,408 and 4,336,148.

The invention thus further relates to a process for the preparation of complex compounds of formula II, which comprises reacting (a) one molar equivalent of a metal salt, semi-metal salt, metal or semi-metal hydroxide, metal or semi-metal oxide, or of a protic acid of the formula

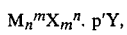

wherein M, X, Y, m and n are as defined for formula II and p' independently of p is a value from 0 to 10, with q molar equivalents of a compound of formula I, and removing any solvent employed, or (b) reacting the reaction product obtained in (a) with a compound of the cation M or of the anion X to replace the cation M or anion X by another cation or anion by means of an ion substitution reaction, or (c) reacting a metal alcoholate or semi-metal alcoholate of M or a protic oxyacid ester with q molar equivalents of a compound of formula I and reacting the resultant complex compound (α) in stoichiometric proportion with an acid of formula $H_nX^n$ or with an ammonium salt $A_nX^n$, wherein A is an ammonium cation, and removing the alcohol, amine or ammonia which has formed, or (β) with a stoichiometric amount of an acid anhydride, acid halide or acid ester of an acid from which the radical X is derived, and removing the alcohol which has formed.

Process variant (a) may be termed a "direct process", as the salt, hydroxide, oxide or the acid is reacted direct with a compound of formula I. The process may be carried out without a solvent, but preferably in a solvent, e.g. in water, an aqueous-organic system or in an organic solvent. The reaction temperature is preferably in the range from 0° to 150° C., in particular from 15° to 100° C., e.g. from 20° to 50° C. The solvent system employed is conveniently removed after formation of the complex, e.g. by distillation.

In variant (b), a complex of formula II is converted by an ion substitution reaction into another complex. This is expedient if, for example, the salt or the acid which it is desired to complex is insufficiently soluble in a solvent system to be employed or if the direct complexing does not proceed satisfactorily. The exchange reaction can take the form of e.g. an ion substitution reaction or a neutralisation reaction. In this manner it is possible to exchange either the anion X or the cation M for another anion or cation in a complex of formula I. Reaction conditions and reaction media correspond to those of reaction (a).

Process variant (c) is particularly suitable if the compounds of a cation X which are to be complexed are insufficiently soluble in the solvent to be employed or if the direct complexing does not proceed satisfactorily. In this case a start is made from an alcoholate of the cation M or from an ester of a protic oxyacid. As already described, either the alcoholate ion or the oxyacid ester is exchanged in the resultant complex. The preferred reaction conditions correspond to those for reactions (a) and (b).

In variant (b), for example, the anhydrous metal salt or semi-metal salt or protic acid is reacted direct with the complexing compounds of formula I. The reaction is accelerated by heating. When using crystalline compounds of formula I, it is expedient to choose a reaction temperature above their melting point, provided no solvent is used. The reaction is complete after the salt has dissolved. Any insoluble constituents can subsequently be filtered off. Examples of anhydrous salts are: $MgCl_2$, $CaCl_2$, $ZnCl_2$, $SnCl_2$, $SnBr_2$, $MnCl_2$ and $CuCl_2$. Gaseous acids such as HCl or HBr can be introduced into the compounds of formula I which have been charged to the reactor.

Another variant of the process comprises using the metal salts or semi-metal salts containing water of crystallisation, or acids, and reacting them with the complexing compounds of formula I. In this process, the water of crystallisation can be removed by heating, under normal or reduced pressure, or expelled by azeotropic distillation with an organic solvent such as a hydrocarbon, e.g. hexane, heptane, petroleum ether, or benzene, toluene, xylene or chloroform.

In yet another process variant, the compounds of formula I are obtained by dissolving the anhydrous salts or the salts which contain water of crystallisation, or the acids, in a suitable organic solvent and then adding a complexing compound of formula I. After removing the solvent, the desired product is obtained. In this process, the water of crystallisation is usually removed along with the solvent. Preferred solvents are those which are also able to dissolve the compound of formula I. Examples of suitable solvents are ethers such as diethyl ether, tetrahydrofuran, alcohols such as methanol and ethanol, and chloroform, dimethylformamide, dimethylsulfoxide or acetonitrile, and suitable salts are KI, NaBr, $AgNo_3$, $CuSO_4.5H_2O$, $Na_2S_2O_3.5H_2O$ and $Cd(CH_3COO)_2.2H_2O$.

In a preferred variant of the process, complex compounds of formula II, in which X is hydroxyl, are prepared by reacting a metal hydroxide or metal oxide or a hydrate thereof with q moles per mole of hydroxide or oxide with a complexing compound of formula I and subsequently adding enough water that the number of hydroxyl groups corresponding to the valency of the metal cation remain. When using a metal oxide, it is probable that initially an alcoholate is formed, with elimination of water, and is hydrolysed again by the water of reaction.

In this reaction it is preferred to use those metal oxides and hydroxides which have a $pK_b$ value not greater than 9, preferably not greater than 4.5, in aqueous solution. Negative values indicate very strong bases. Examples are the metal oxides and hydroxides of alkali metals and alkaline earth metals, of univalent tallium and of silver.

The processes employing the protic acids do not basically differ in kind. Thus the protic acids to be complexed can be added direct to the complexing compound of formula I, without a solvent or in the presence of a solvent such as a hydrocarbon. As in the subsequent reaction, it is convenient to cool the reaction mixture until a clear solution forms, so as not to exceed temperatures up to 50° C. When using dilute aqueous protic acids, it is advantageous to remove the water in the presence of a complexing compound of formula I by azeotropic distillation, and a solvent may also be used.

In the compounds $H_nX$ and $A_nX$, n is preferably an integer from 1 to 3 and the $pK_a$ value of the acid is not greater than 15.8, preferably not greater than 7 and, most preferably, not greater than 4. By way of explanation it should be mentioned that the $pK_a$ value of 15.8 includes water as the weakest acid.

In all variants of the process, the reaction can be carried out in the presence of a solvent or without a solvent. Particularly suitable organic solvents are ethers such as diethyl ether, alcohols such as methanol, ethanol, and preferably hydrocarbons such as pentane, hexane, benzene, toluene and xylene, which can be readily removed from the reaction mixture by distillation, under normal or reduced pressure, to obtain pure complexed compounds of the invention. Before distillation, any insoluble constituents can be removed by filtration. Further examples of solvents are acid amides, e.g. dimethylformamide, dimethylacetamide, formamide, and also sulfoxides and sulfones, e.g. dimethylsulfoxide, dimethylsulfone and tetramethylsulfone.

The process is conveniently carried out at ambient temperature (about 20° C.) up to temperature of 150° C., preferably up to 50° C. When adding the reactants (anhydrous protic acids, acid anhydride, acid ester, acid halide), a strong exothermic reaction is usually observed. It may therefore sometimes be expedient to cool the reaction mixture. To remove the solvent it is necessary to heat the reaction mixture. Similar preferred reaction conditions also apply to process variant (b).

The metal, semi-metal and oxymetal alcoholates employed for process variant (c) may be prepared by different known methods. Attention is drawn in this connection e.g. to the possibilities disclosed in U.S. Pat. No. 4,404,408, column 14, line 38 to column 15, line 30. Further details will be found in U.S. Pat. No. 4,404,408, column 15, line 31 to column 20, line 19, in which connection for "Z" in each case read "compound of formula I". The cited pages shall be considered as part of the description of this specification. It is also to be borne in mind that the integer q in the complex compounds of this invention is smaller than in those disclosed in U.S. Pat. No. 4,404,408.

The complex compounds of formula II are of crystalline, wax-like, mobile or viscous consistency, depending on the anions, cations and complexing compounds of formula I and in what ratio they are present. They have a remarkably high thermal stability, which indicates that the complexing compounds of formula I are relatively firmly bonded. This statement is supported by the fact that many representatives are crystalline compounds that can be recrystallised from suitable solvents without any change in their composition.

An especially notable property is the surprisingly good solubility of the compounds of formula II in many organic solvents, even in nonpolar, aprotic solvents such as liquid hydrocarbons. By choice and number of the complexing compounds of formula I it is possible to influence the solubility. The compatibility with natural and synthetic polymers, lubricants, fuels and hydraulic fluids is also very good.

The compounds of formula II have very good antistatic and stabilising properties.

Accordingly, the present invention also relates to compositions comprising a natural or synthetic polymer, a natural or synthetic lubricant, fuel or hydraulic fluid as well as at least one complex compound of formula II.

Examples of natural and synthetic polymers in compositions of this invention are:

1. Polymers of monoolefines and diolefines, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under (1), for example mixtures of polypropylene with polyisobutylene.

3. Copolymers of monoolefines and diolefines with each other or with other vinyl monomers, such as, for example, ethylene/propylene, propyene/butene-1, propylene/isobutylene, ethylene/butene-1, propylene/butadiene, isobutylene/isoprene, ethylene/alkyl acrylates, ethylene/alkyl methacrylates, ethylene/vinyl acetate or ethylene/acrylic acid copolymers and their salts (ionomers) and terpolymers of ethylene with ppropylene and a diene, such as hexadiene, dicyclopentadiene or ethylidene-norbornene.

4. Polystyrene, poly-(p-methylstyrene).

5. Copolymers of styrene or α-methylstyrene with dienes or acrylic derivatives, such as, for example, styrene/butadiene, styrene/acrylonitrile, styrene/ethyl methracrylate, styrene/butadiene/ethyl acrylate, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene//styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, epichlorohydrine homo- and copolymers, polymers from halogen-containing vinyl compounds, as for example, polyvinylchloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from $\alpha\beta$-unsaturated acids and derivatives thereof, such as polyacrylates and polymethacrylates, polyacrylamide and polyacrylonitrile.

9. Copolymers from the monomers mentioned under (8) which each other or with other unsaturated monomers, such as, for instance, acrylonitrile/butadien, acrylonitrile/alkyl acrylate, acrylonitrile/alkoxyalkyl acrylate or acrylonitrile/vinyl halogenide copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallyl-melamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer.

13. Polyphenylene oxides and sulfides, and mixtures of polyphenylene oxides with polystyrene.

14. Polyurethanes which are derived from polyethers, polyesters or polybutadiens with terminal hydroxyl groups on the one side and aliphatic or aromatic polyisocyanates on the other side, as well as precursors thereof (polyisocyanates, polyols or prepolymers).

15. Polyamides and copolyamides which are derived from diamines and dicarboxylic acids and/or from aminocarboxylic acids or the corresponding lactams, such as polyamide 4, polyamide 6, polyamide 6/6, polyamide 6/10, polyamide 11, polyamide 12, poly-2,4,4,-trimethylhexamethylene terephthalamid or poly-m-phenylene isophthalamide, as well as copolymers thereof with polyethers, such as for instance, with polyethylene glycol, polypropylene glycol or polytetramethylene glycols.

16. Polyureas, polyimides and polyamide-imides.

17. Polyesters which are derived from dicarboxylic acids and diols and/or from hydroxycarboxylic acids or the corresponding lactones, such as polyethylene terephthalate, polybutylene terephthalate, poly-1,4-dimethylol-cyclohexane terephthalate, poly-[2,2,-(4-hydroxyphenyl)-propane] terephthalate and polyhydroxybenzoates as well as block-copolyether-esters derived from polyethers having hydroxyl end groups.

18. Polycarbonates and polyester-carbonates.

19. Polysulfones, polyethersulfones and polyetherketones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low inflammability.

23. Thermosetting acrylic resins, derived from substituted acrylic esters, such as epoxy-acrylates, urethane-acrylates or polyesteracrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides.

26. Natural polymers, such as cellulose, rubber, gelatine and derivatives thereof which are chemically modified in a polymerhomologous manner, such as cellulose acetates, cellulose propionates and cellulose butyrates, or the cellulose ethers, such as methylcellulose.

27. Mixtures of polymers as mentioned above, for example PP/EPDM, polyamide 6/EPDM or ABS, PVC/EVA, PVC/ABS, PVC/MBS, PC/ABS, PBTP/ABS.

28. Naturally occuring and synthetic organic materials which are pure monomeric compounds or mixtures of such compounds, for example mineral oils, animal and vegetable fats, oil and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

29. Aqueous emulsions of natural or synthetic rubber, e.g. natural latex or latices of carboxylated styrene/-butadiene copolymers.

Examples of compositions of this invention are those which contain a thermoplastic and at least one complex compound of formula I, as well as those which contain an elastomer and at least one complex compound of formula II.

The compositions which contain polymers of the above classes may additionally contain further different conventional additives, e.g. the antioxidants of classes 1 to 9 listed above for the use of compounds of formula I as well as one or more of the following additives:

2. UV absorbers and light stabilisers 2.1. 2-(2'-Hydroxyphenyl)-benztriazoles, for example, 5'-methyl-, 3',5'-di-tert-butyl-, 5'-tert-butyl-, 5'-(1,1,3,3-tetramethylbutyl)-, 5-chloro-3',5'-di-tert-butyl-, 5'-chloro-3'-tert-butyl-5'-methyl-, 3'-sec-butyl-5'-tert-butyl-, 4'-octoxy-, 3',5'-di-tert-amyl derivative.

2.2. 2-Hydroxy-benzophenones, for example, the 4-hydroxy-, 4-methoxy-, 4-octoxy, 4-decyloxy-, 4-dodecyloxy-, 4-benzyloxy, 4,2',4'-trihydroxy-and 2'-hydroxy-4,4'-dimethoxy derivatives.

2.3. Esters of substituted and unsubstituted benzoic acids, for example, phenyl salicylate, 4-tert.butylphenylsalicilate, octylphenyl salicylate, dibenzoylresorcinol, bis-(4-tert.butylbenzoyl) -resorcinol, benzoyl resorcinol,3,5-di-tert-.-butyl-4-hydroxybenzoic acid, 2,4-di-tert.butyl-phenyl ester and 3,5-di-tert-. -butyl-4-hydroxybenzoate.

2.4. Acrylates, for example ethyl α-cyano-β, β-diphenylacrylate, methyl 2-carbomethoxycinnamate, methyl α-cyano-β-methyl-p-methoxy-cinnamate, butyl α-cyano-β-methyl-p-methoxy-cinnamate, methyl α-carbomethoxy-p-methoxy-cinnamate and N-(β-carbomethoxy-β-cyano-vinyl) -2-methyl-indoline.

2.5 Nickel compounds, for example, nickel complexes of 2,2'-thiobi-bis -[4-(1,1,3,3-tetramethylbutyl)-phenol], such as the 1:1 or 1:2 complex, with or without additional ligands such as n-butylamine, triethanolamine or N-cyclohexyl-diethanolamine, nickel dibutyldithiocarbamate, nickel salts of 4-hydroxy-3,5-di-tert-butylbenzyl-phosphonic acid monoalkyl esters, e.g. of the methyl, ethyl or butyl ester, nickel complexes of ketoximes, e.g. of 2-hydroxy-4-methyl-phenyl undecyl ketoneoxime, nickel complexes of 1-phenyl-4-lauroyl-5-hydroxypyrazole, with or without additional ligands.

2.6 Sterically hindered amines, for example bis-(1,2,2,6,6-tetramethylpiperidyl)-sebacate, bis-(1,2,2,6,6-pentamethylpiperidyl)-sebacate, bis-(1,2,2,6,6-pentamethylpiperidyl)-n-butyl-3,5di-tert-butyl-4-hydroxybenzyl-malonate, the condensation product of 1hydroxyethyl-2,2,6,6-tetramethyl-4-hydroxypiperidine and succinic acid, the condensation product of N,N'-(2,2,6,6-tetramethylpiperidyl)-hexamethylenediamine and 4-tert-octylamino-2,6-dichloro-1,3,5-a-triazine, and tris-(2,2,6,6-tetramethylpiperidyl)-nitrilotriacetate.

2.7. Oxalic acid diamides, for example, 4,4'-dioctyloxyoxanilide, 2,2'-dioctyloxy-5,5'-di-tert-butyloxanilide, 2,2'-di-dodecyloxy-5,5'-di-tert-butyloxanilide, 2-ethoxy-2'-ethyloxanilide, N,N'-bis-(3-dimethylaminopropyl)oxalamide, 2-ethoxy-5-tert-butyl-2'-ethyloxanilide and its mixture with 2-ethoxy-2'-ethyl-5,4'-di-tert-butyloxanilide and mixtures of ortho-and para-methoxy-disubstituted and mixtures of o -and p-ethoxy-disubstituted oxanilides.

3. Metal deactivators, for example N,N'-diphenyloxalic acid diamide, N-salicylal-N'-salicyloylhydrazine, N,N'-bis-salicyloylhydrazine, N,N'-bis-(3,5-di-tert.butyl-4-hydroxyphenylpropionyl)-hydrazine, 3-salicyloylamino-1,2,4-triazole, bis-benzylidene-oxalic acid dihydrazide.

4. Phosphites and phosphonites, for example triphenyl phosphite, diphenylalkyl phosphites, phenyldialkyl phosphites, tri(nonylphenyl) phosphite, trilauryl phosphite, trioctadecyl phosphite, distearylpentaerythritol diphosphite, tris-(2,4-di-tert-butylphenyl) phosphite, diisodecylpentaerythritol diphosphite, di-(2,4-di-tert-butylphenyl)pentaerythritol diphosphite, tristearylsorbitol triphosphite, tetrakis-(2,4-di-tert.butylphenyl)-4,4'-biphenylene diphosphite, 3,9-bis-(2,4-di-tert-butylphenoxy-2,4,8,10-tetraoxa-3,9-diphosphaspiro[5.5]undecane.

5. Peroxide scavengers, for example esters of β-thiodipropionic acid, for example the lauryl, stearyl, myristyl or tridecyl esters, mercaptobenzimidazole or the zinc salt of 2-mercaptobenzimidazole, zincdibutyldithiocarbamate, dioctadecyldisulfide, pentaerythritoltetrakis -(β-dodecylmercapto)propionate.

6. Polyamide stabilisers, for example, copper salts in combination with iodides and/or phosphorus compounds and salts of divalent manganese.

7. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, manganese stearate, sodium ricinoleate and potassium palmitate, antimony pyrocatechoate or tin pyrocatechoate.

8. Nucleating agents, for example, 4-tert-butylbenzoic acid, adipic acid, diphenylacetic acid.

9. Fillers and reinforcing agents, for example calcium carbonate, silicates, glass fibres, asbestos, talcum, kaolin, mica, barium sulfate, metal oxides and hydroxides, carbon black, graphite.

10. Other additives, for example plasticisers, lubricants, emulsifiers, pigments, fluorescent whitening agents, flame retardants, antistatic agents, blowing agents.

Further examples of compositions of this invention are those comprising a lubricant or hydraulic fluid and at least one complex compound of formula II.

Typical lubricants and hydraulic fluids are those that have already been described herein as suitable for the incorporation of compounds of formula I. In addition to containing compounds of formula II, the lubricant and hydraulic fluid compositions may also contain other additives for further improving the basic properties of lubricants. Such additives comprise: antioxidants, metal deactivators, rust inhibitors, viscosity index improvers, pour-point depressors, dispersants, surfactants, extreme pressure additives and antiwear additives. Examples of such additives are those previously listed in this description on pages 6–10 in respect of compositions containing compounds of formula I.

The compounds of formula II are preferably added to the polymer, lubricant, fuel and hydraulic fluid compositions in an amount of 0.001 to 15% by weight, in particular 0.01 to 10% by weight and, most preferably, 0.01–5% by weight, for example 0.01 to 3% by weight.

The invention therefore also relates to the use of complex compounds of formula I as stabilisers and antistatic agents for natural and synthetic polymers as well as for natural or synthetic lubricants, fuels or hydraulic fluids.

The preferred utility of complex compounds of formula II is as stabilisers and antistatic agents in thermoplastics and elastomers, and also as extreme pressure and antiwear additives in lubricants and hydraulic fluids.

When used as stabilisers, the compounds of formula II are e.g. effective thermostabilisers (processing stabilisers) and performance stabilisers (e.g. antioxidants). They are also effective extreme pressure and antiwear additives for lubricants and hydraulic fluids. Examples of the thermoplastic polymers, elastomers, lubricants and hydraulic fluids to which they are added are listed above.

The invention is illustrated in more detail by the following Examples. Parts and percentages are by weight, as they are throughout the description and in the claims.

Example 1

18.1 g of aminosorbitol, 29.2 g of 1-(t-butylthio)-2,3-epoxypropane and 100 ml of methanol are stirred under reflux for 2 hours. A slight turbidity is clarified by filtration and the volatile constituents are distilled off by rotary evaporation, affording 47.0 g (99% of theory) of the compound of formula $$CH_2-CH-CH-CH-CH-CH_2-N(-CH_2-CH-CH_2-S-{}^tC_4H_9)_2$$
$$\quad\ \ |\quad\ |\quad\ |\quad\ \ \ |\qquad\qquad\qquad\ \ |$$
$$\ \ \ \ OH\ \ OH\ OH\ \ \ \ OH\qquad\qquad\qquad OH$$

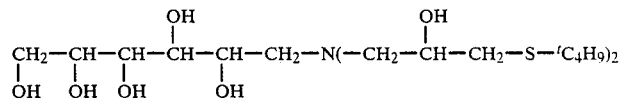

as a highly viscous substance; $n_D^{40}$: 1.5202.

Example 2

9 g (0.05 mole) of aminosorbitol, 23.8 g (0.11 mole) of 1-(t-nonylthio)-2,3-epoxypropane, 20 ml of methanol and 20 ml of tetrahydrofuran are refluxed at 64° C. until a clear solution is obtained. A slight turbidity is removed by filtration and the mixture is diluted with 32.8 g of paraffin oil and the volatile constituents are distilled off by rotary evaporation, affording 65.4 g (100% of theory) of the compound of formula

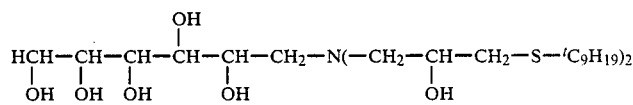

as a viscous liquid; $n_D^{20}$: 1.4876.

Examples 3–9

Further compounds are prepared in accordance with the particulars of Example 1 and are listed in Table 1.

TABLE 1

| Example | Formula | Refractive index $n_D^{20}$ | Comments |
|---|---|---|---|
| 3 | HCH—CH—CH—CH—CH—CH$_2$—N(—CH$_2$—CH—CH$_2$—S—$^tC_{12}H_{25})_2$ with OH groups | 1.5086 | |
| 4 | HCH—CH—CH—CH—CH—CH$_2$—N—CH$_2$—CH—CH$_2$—S—$^tC_{16}H_{33}$ with OH groups and N-CH$_3$ | 1.4825 in paraffin oil 1:1 | product: tarry substance |

TABLE 1-continued

| Example | Formula | Refractive index $n_D^{20}$ | Comments |
|---|---|---|---|
| 5 | HCH—CH—CH—CH—CH—CH$_2$—N(CH$_3$)—CH$_2$—CH(OH)—CH$_2$—S—$^t$C$_{12}$H$_{25}$ with OH groups on positions 1,2,3,4 and OH on carbon bearing N-CH$_2$ | | product: tarry substance |
| 6 | HCH—CH—CH—CH—CH—CH$_2$—N(C$_2$H$_5$)—CH$_2$—CH(OH)—CH$_2$—S—$^t$C$_{12}$H$_{25}$ with OH, OH, OH, OH | 1.4972 | |
| 7 | HCH—CH—CH—CH—CH—CH$_2$—N(—CH$_2$—CH(OH)—CH$_2$—O—$^i$C$_8$H$_{17}$)$_2$ with OH, OH, OH, OH | 1.4734 | |
| 8 | HCH—CH—CH—CH—CH—CH$_2$—N(—CH$_2$—CH(OH)—$^n$C$_{10}$H$_{21}$)$_2$ with OH, OH, OH, OH | 1.4728 in paraffin oil 1:1 | product: tarry substance |
| 9 | HCH—CH—CH—CH—CH—CH$_2$—N(—CH$_2$—CH(OH)—S—C$_2$H$_5$)$_2$ with OH, OH, OH, OH | | |

N-Methylaminosorbitol and N-ethylaminosorbitol and the corresponding 1-alkylthio-2,3-epoxypropane are used in approximately equimolar amount in the preparation of compounds 4, 5 and 6.

Example 10

3.6 g of NiCl$_2$.6H$_2$O are dissolved in 50 ml of methanol and to the solution are added 10.5 g of the reaction product of aminosorbitol and 1-(t-dodecylthio)-2,3-epoxypropane obtained in Example 3. The solvent is distilled off under reduced pressure. The residual water of crystallisation is removed quantitatively with toluene at 40° C. under reduced pressure, affording 12.5 g of the complex compound of the formula

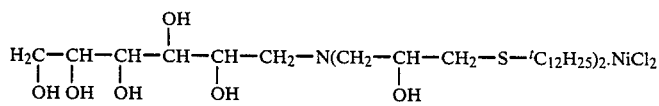

as a pale green resinous substance which is readily soluble in heptane and other nonpolar solvents. A 50% solution has a refractive index $n_D^{40}=1.4866$.

Example 11

If CuSO$_4$.5H$_2$O is used instead of NiCl$_2$.6H$_2$O in Example 10, the complex compound of formula

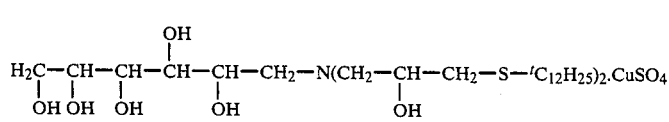

is obtained in a yield of 12.9 g as a bluish green glassy substance which dissolves readily in heptane and other nonpolar solvents. A 50% solution in paraffin oil has a refractive index $n_D^{40}=1.4836$.

Example 12

10 g of Cu(OOCCH$_3$)$_2$.H$_2$O are disolved in methanol and 27.7 g of the reaction product of aminosorbitol and 1-(isooctyloxy)-2,3-epoxypropane obtained in Example 7 are added. Then 4.9 g of phosphoric acid are added and the solvent is distilled off under vacuum in a rotary evaporator. The residual liberated acetic acid is removed quantitatively with toluene under vacuum, affording 31.5 g of the compound of formula

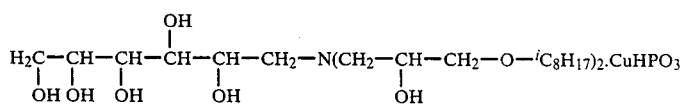

as a turquoise glassy substance which is readily soluble in toluene and xylene. A 50% solution in xylene as a refractive index $n_D^{50}=1.4846$.

Example 13

34.9 g of the reaction product of aminosorbitol and 1-(t-dodecylthio)-2,3-epoxypropane obtained in Example 3 are dissolved in 200 ml of toluene. To the solution are added 15.8 g of Ba(OH)$_2$.8H$_2$O and 9 ml of water of crystallisation/water of reaction are distilled off, with stirring. With cooling, a mixture of a further 34.9 g of the product of Example 3 and 5.8 g of sulfuric acid monohydrate is then added dropwise at 20° C. The mixture is stirred for 15 minutes at 20° C. and the solvent is distilled off under vacuum, affording 81 g of the compound of formula

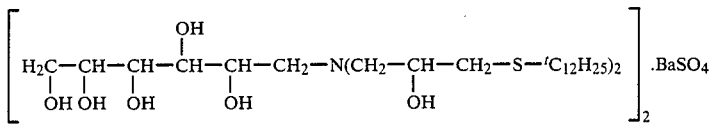

as a highly viscous substance which is readily soluble in toluene, xylene and other nonpolar solvents.

Example 14

2.5 g of orthophosphoric acid are dissolved in methanol and to the solution are added 15.3 g of the reaction product of aminosorbitol and 1-(t-nonylthio)-2,3-epoxypropane obtained in Example 2. The solvent is removed under reduced pressure, affording 17.8 g of the compound of formula

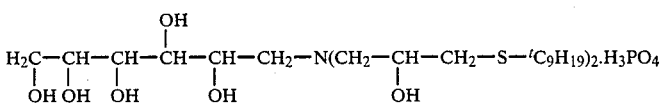

as a resinous substance which is readily soluble in xylene. A 50% solution in xylene has a refractive index $n_D^{20} = 1.5407$.

The compound of formula

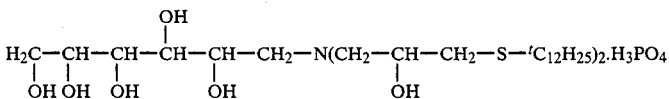

is obtained in corresponding manner using the product of Example 3. A 50% solution in xylene has a refractive index $n_D^{20} = 1.5029$.

Further compounds of formula II can be prepared in accordance with the particulars of U.S. Patent 4,404,408, column 23, line 32 to column 26, line 14.

Examples of further compounds of the formula $M_n{}^m \cdot X_m{}^n \cdot Y$, which can be reacted with compounds of formula I to give complexes of formula II (e.g. in accordance with Examples 10–14 or the aforementioned methods A-F7) are listed in Table 1 of U.S. Pat. No. 4,404,408 (columns 25–40), left hand column of the Table ("salts", Examples 1–204).

Use Example 1

The weld load (WL) and the wear scar diameter (WSD) are determined using the Shell four-ball machine (IP 239/73, Extreme Pressure and Wear Lubricant Test for Oils and Greases, Four-Ball Machine) as a function of the concentration of the extreme pressure additive.

WL = weld load: the load at which the 4 balls become welded together within 10 seconds WSD = wear scar diameter: the average diameter of the scars produced on the 3 immobile balls after 10 minutes at a load of 400 N.

The test fluid employed is a mineral oil of viscosity class ISO VG 100. The results are reported in Table 2.

TABLE 2

| Additive Example No. | Concentration (% by weight) | WL [N] | WSD [mm] |
|---|---|---|---|
| base oil without additive | — | 1450 | 0.85 |
| 3 | 0.25 | | 0.45 |
| | 1.0 | 1700 | 0.45 |
| | 2.5 | | 0.45 |
| | 5.0 | 1900 | 0.45 |
| 4 | 0.25 | 1700 | 0.50 |
| | 1.0 | 1800 | 0.50 |

Use Example 2

The WL and WSD values for water (adjusted to pH 8.5 with triethylamine) are determined by means of the apparatus described in Use Example 1 with and without an additive of formula I.

The test results are reported in Table 3.

TABLE 3

| Additive Example | Concentration additive (% by weight) | Concentration triethylamin (% by weight) | pH | WL (N) | WSD (nm) |
|---|---|---|---|---|---|
| water without additive | — | 0.6 | 8.5 | <1200 | >1.5 |
| 1 | 2.5 | 0.6 | 8.5 | 1900 | 0.75 |

In the tests of Use Examples 1 and 2, and 5–9. Very good WL and WSD values are also obtained with the compounds of Examples 10 to 14, especially in the tests described in Use Example 1.

What is claimed is:

1. A composition comprising about 0.01 to 5% by weight of a hydraulic fluid and least one compound of the formula

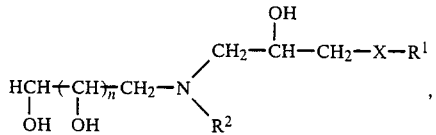

(I)

wherein n is 2, 3 or 4, X is —S—, —O—, —O—CO— or —CH$_2$—, R$^1$ is C$_1$-C$_{22}$alkyl, C$_5$-C$_6$cycloalkyl or phenyl, and R$^2$ is hydrogen, C$_1$-C$_8$alkyl, C$_2$-C$_4$alkyl which is substituted by an —OH group, or a group of the formula —CH$_2$—CH(OH)—CH$_2$—X—R$^1$ have the given meanings.

2. A composition according to claim 1 which contains a compound of formula I, wherein X is —S—, —CH$_2$— or —O—, R$^1$ is straight chain or branched C$_5$-C$_{16}$alkyl, R$^2$ is methyl, ethyl or the group —CH$_2$—CH(OH)—CH$_2$—X—R$^1$, wherein X and R$^1$ have the given meanings and n is 4.

3. A composition according to claim 1 which contains a compound of formula I, wherein n is 4.

4. A composition according to claim 3 which contains a compound of formula I, wherein R$^2$ is methyl or ethyl.

5. A composition according to claim 1 which contains a compound of formula I, wherein X is —S—.

6. A composition according to claim 1 which contains a compound of formula I, wherein R$^2$ is a group of formula —CH$_2$—CH(OH)—CH$_2$—X—R$^1$.

7. A composition according to claim 1 which contains a compound of formula I, wherein R$^1$ is C$_8$-C$_{12}$alkyl.

* * * * *